(12) United States Patent
Brandesky

(10) Patent No.: US 8,191,437 B2
(45) Date of Patent: Jun. 5, 2012

(54) GAS SAMPLE COLLECTION AND ANALYSIS

(75) Inventor: Joseph A. Brandesky, College Station, TX (US)

(73) Assignee: O.I. Corporation, College Station, TX (US)

(*) Notice: Subject to any disclaimer, the term of this patent is extended or adjusted under 35 U.S.C. 154(b) by 299 days.

(21) Appl. No.: 12/121,589

(22) Filed: May 15, 2008

(65) Prior Publication Data
US 2008/0307903 A1 Dec. 18, 2008

Related U.S. Application Data

(60) Provisional application No. 60/917,955, filed on May 15, 2007.

(51) Int. Cl.
G01N 1/00 (2006.01)
G01N 1/12 (2006.01)

(52) U.S. Cl. ................... 73/864.83; 73/864.62

(58) Field of Classification Search ............... 73/864.83, 73/864.81, 864.62
See application file for complete search history.

(56) References Cited

U.S. PATENT DOCUMENTS

| | | | |
|---|---|---|---|
| 3,904,368 A | | 9/1975 | Takeyama et al. |
| 4,008,393 A | * | 2/1977 | Rapkin .................. 436/59 |
| 4,336,127 A | | 6/1982 | Bertelson |
| 5,080,865 A | * | 1/1992 | Leiner et al. ............ 422/68.1 |
| 5,142,143 A | * | 8/1992 | Fite et al. ............... 250/288 |
| 5,303,599 A | | 4/1994 | Welker |
| 5,932,791 A | | 8/1999 | Hambitzer et al. |
| 5,981,912 A | * | 11/1999 | Gilmutdinov et al. ........ 219/398 |
| 6,016,841 A | | 1/2000 | Larsen |
| 7,225,690 B1 | * | 6/2007 | Mayeaux .............. 73/864.62 |
| 2002/0064881 A1 | * | 5/2002 | Devlin et al. ............ 436/43 |
| 2005/0177056 A1 | | 8/2005 | Giron et al. |

FOREIGN PATENT DOCUMENTS

WO 2009151864 A1 12/2009

OTHER PUBLICATIONS

PCT International Search Report and Written Opinion for International Application No. PCT/US08/63757 dated Sep. 22, 2008.
International Preliminary Report on Patentability for Appl. No. PCT/US2009/044040 dated Nov. 25, 2010.
International Search Report and Written Opinion of the International Searching Authority for Appl. No. PCT/US2009/044040 dated Jul. 2, 2009.
International Preliminary Report on Patentability for Appl. No. PCT/US2008/063757 dated Nov. 17, 2009.

* cited by examiner

*Primary Examiner* — Hezron E Williams
*Assistant Examiner* — Nathaniel Kolb
(74) *Attorney, Agent, or Firm* — J. Roger Williams, Jr.; Andrews Kurth LLP

(57) ABSTRACT

A system and method for capturing a sample gas for analysis is disclosed. In one embodiment, the system includes an accumulator that has a variable volume. A volume of the sample gas is fed to the accumulator. The system also has an analyzer. An aliquot of the sample gas is withdrawn from the accumulator and fed to the analyzer. The analyzer analyzes a desired component of the sample gas.

5 Claims, 5 Drawing Sheets

GAS SAMPLE COLLECTION AND ANALYSIS

CROSS-REFERENCE TO RELATED APPLICATIONS

This application is a non-provisional application that claims the benefit of U.S. application Ser. No. 60/917,955 filed on May 15, 2007, which is incorporated by reference herein in its entirety.

STATEMENT REGARDING FEDERALLY SPONSORED RESEARCH OR DEVELOPMENT

Not applicable.

BACKGROUND OF THE INVENTION

1. Field of the Invention

This invention relates to the field of chemical analysis and more specifically to the field of sample gas collection and analysis.

2. Background of the Invention

Chemical analysis often includes analyzing the amount of carbon or other elements such as nitrogen in a sample. Conventional practice for detecting carbon or such other elements in samples (i.e., solid, sludge or aqueous samples) employs techniques to convert the element of interest to a gas product prior to making the measurement. For instance, through oxidation or combustion, carbon in the sample may be combined with oxygen to produce carbon dioxide. The gas of interest is typically transferred to a calibrated analyzer (i.e., total organic carbon analyzer) by which the gas of interest is measured in a single-pass measurement to determine the level of product present in the sample. Drawbacks include the inability to store a sample for later analysis. Additional drawbacks with the single-pass measurement include the inability to satisfy a need for multiple analyses of a sample. Further drawbacks to the single-pass measurement include no opportunity to re-test after adjusting system parameters when calibration ranges are exceeded or detection limits are not achieved.

Conventional analyzers use a variety of oxidation techniques including combustion chemical reactions and catalytic reactions to convert target products to the analytical gas for measurement by the analyzer detection system. For instance, an example of a conventional analyzer detector is a nondispersive infrared sensor (NDIR). Drawbacks to current analyzer designs include the limitation of the detector range capability. In addition, direct measurement systems drive operational inefficiencies involving samples with a high concentration of the product of interest and generate gas concentrations above the calibration or saturation points of the detector. Additional inefficiencies include samples with concentrations of the product of interest that are too low to generate gases or with concentrations above the detection limit of the detector.

Consequently, there is a need for an improved process for measuring the level of a component in a sample. Further needs include an improved process that allows for multiple measurements to be made on the gases generated from a single sample. Needs also include an improved process that provides analyzer designs to operate over a broader dynamic range and be fault tolerant to over and under ranging.

BRIEF SUMMARY OF SOME OF THE PREFERRED EMBODIMENTS

These and other needs in the art are addressed in one embodiment by a system for capturing a sample gas for analysis. The system includes an accumulator. The accumulator has a variable volume. A volume of the sample gas is fed to the accumulator. The system also includes an analyzer. An aliquot of the sample gas is withdrawn from the accumulator and fed to the analyzer. The analyzer analyzes a desired component of the sample gas.

These and other needs in the art are addressed in another embodiment by a method for capturing a sample gas for analysis. The method includes feeding the sample gas to an accumulator, wherein the accumulator has a variable volume. The method also includes withdrawing an aliquot of the sample gas from the accumulator. The method further includes feeding the aliquot of the sample gas to an analyzer. In addition, the method includes analyzing a desired component of the sample gas.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
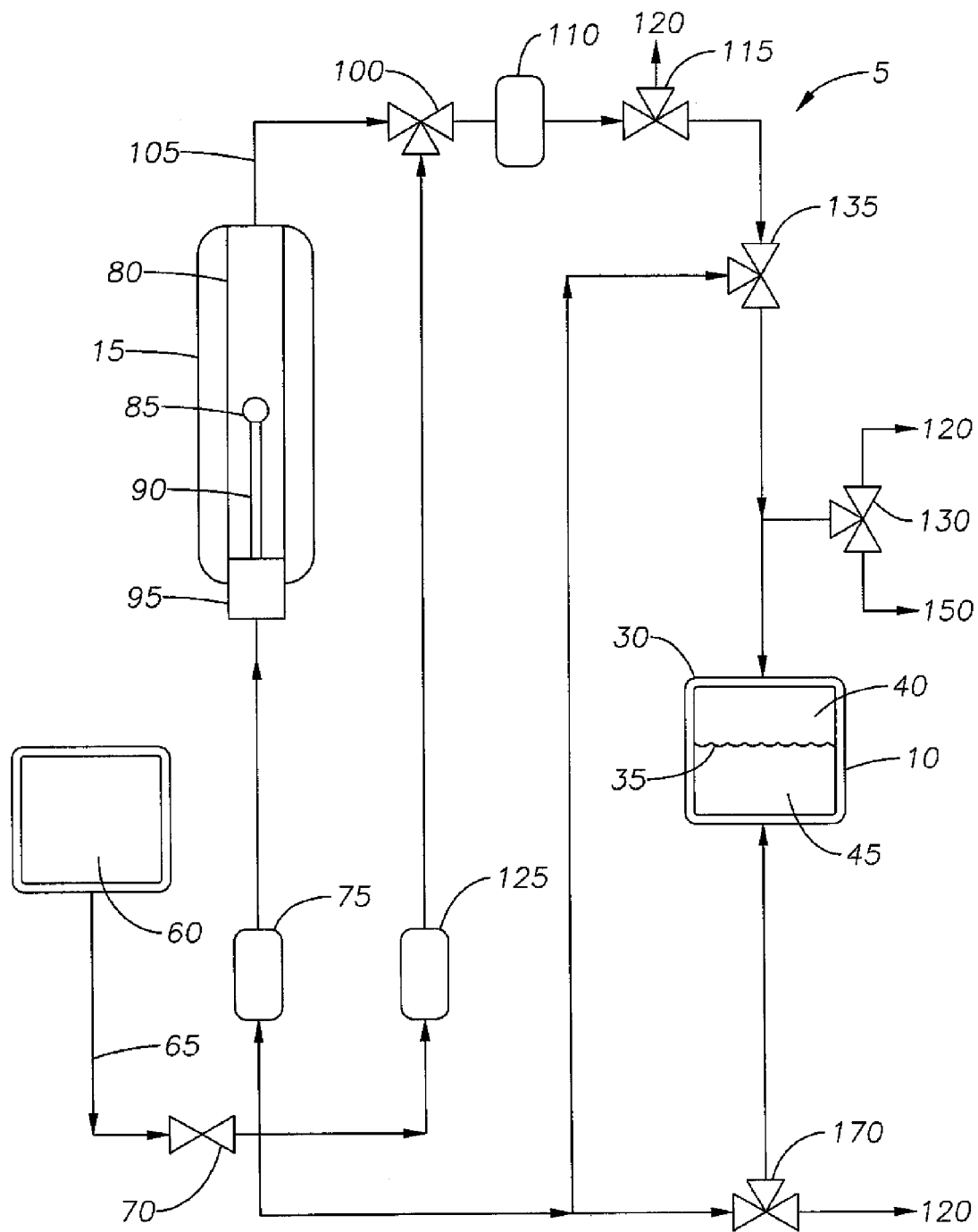
FIG. 1 illustrates a sample analysis process including an accumulator and a sample collection apparatus.
Figure 2:
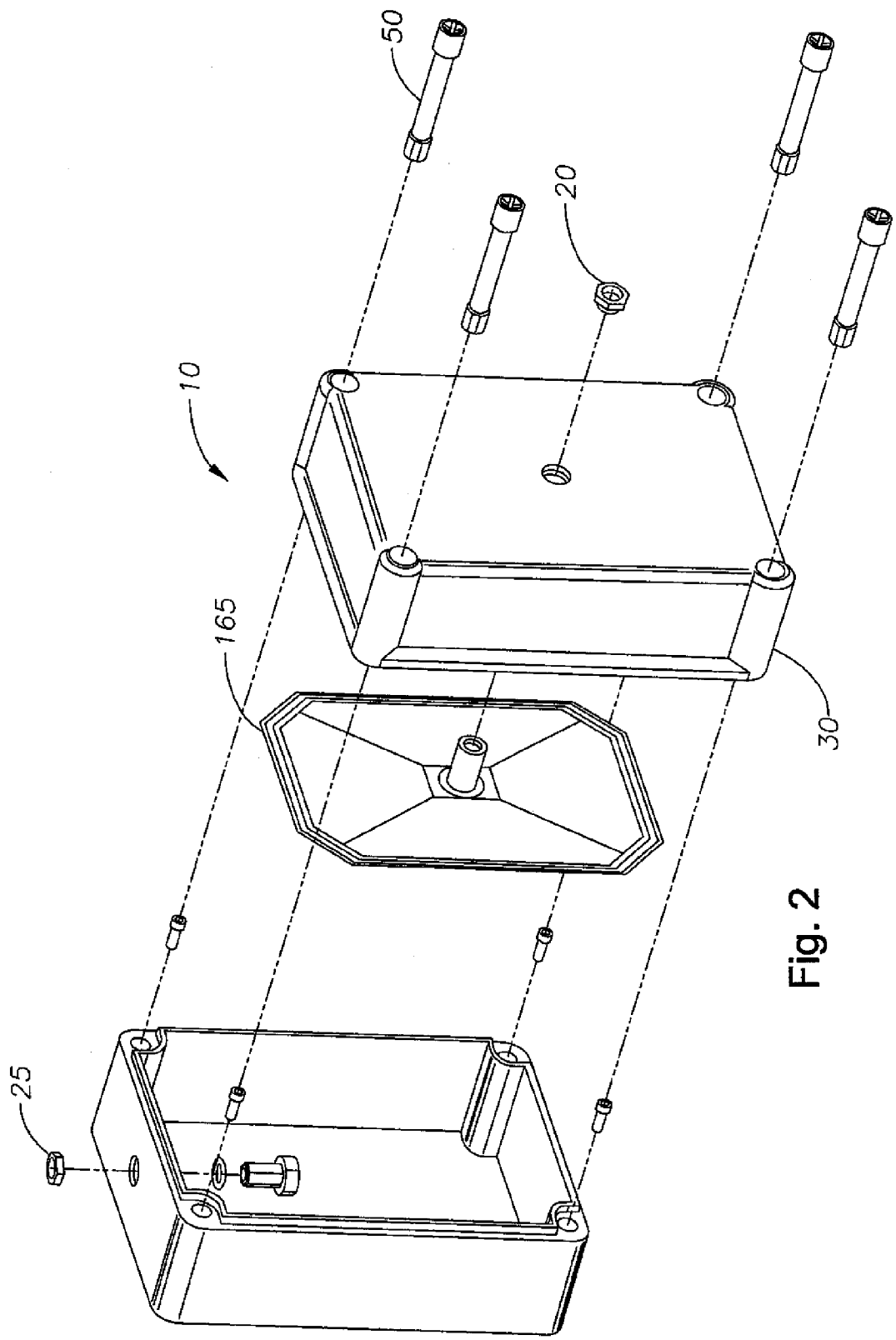
FIG. 2 illustrates an exploded view of an accumulator having a sample side comprising a flexible bag.
Figure 3:
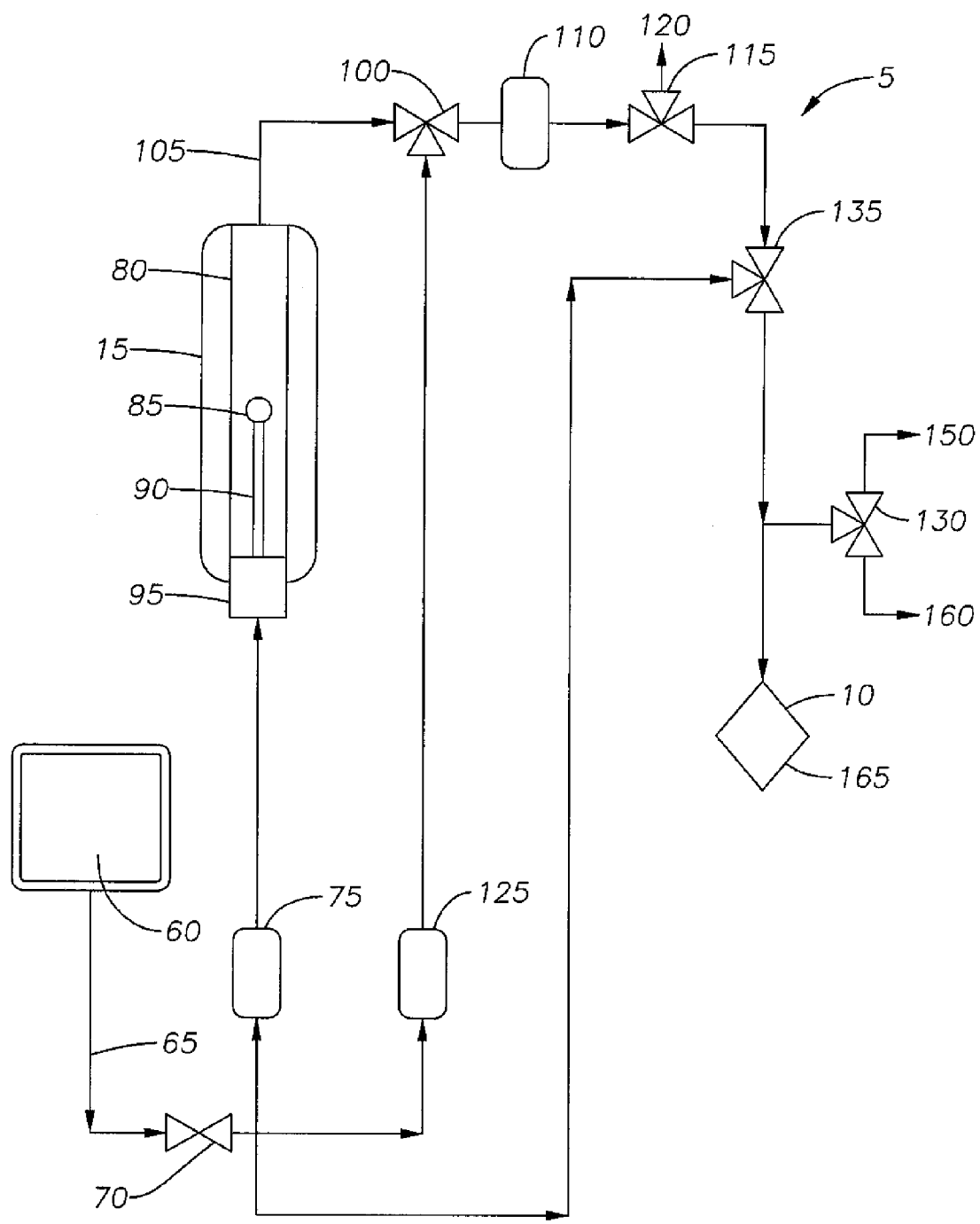
FIG. 3 illustrates a sample analysis process including a sample collection apparatus and an accumulator comprising a flexible bag.

FIG. 1 illustrates a sample analysis process 5 that includes accumulator 10 and sample gas collection apparatus 15. Accumulator 10 is a sealed device suitable for allowing the transfer of sample gases at constant pressure. In embodiments as illustrated in FIGS. 1 and 2, accumulator 10 has a sealed chamber 30 that includes a chamber separator 35 or a flexible bag 165. In alternative embodiments as illustrated in FIG. 3, accumulator 10 is a flexible bag 165. Accumulator 10 has a variable volume by which a variable volume of sample gas 105 may be contained. It is to be understood that in FIG. 1 accumulator 10 is illustrated in a cross sectional side view.

In an embodiment as illustrated in FIG. 1, accumulator 10 includes chamber 30, chamber separator 35, sample side 40, and pressure side 45. Chamber separator 35 is a flexible membrane that separates sample side 40 from pressure side 45 and prevents the flow of any gas between sample side 40 and pressure side 45. Chamber separator 35 is secured to chamber 30 by any suitable means.

FIG. 2 illustrates an exploded perspective view of an embodiment of accumulator 10 in which accumulator 10 includes flexible bag 165. In such embodiment, flexible bag 165 is attached to sample orifice 20 to allow sample gas 105 to flow in and out of flexible bag 165.

Chamber separator 35 and flexible bag 165 are flexible membranes that are impermeable by gas. In embodiments, chamber separator 35 and flexible bag 165 are flexible and impermeable by gas but are non-elastic. Without being limited by theory, elastic deformation of chamber separator 35 or flexible bag 165 may impart varying pressure on sample gas 105, and in some embodiments a constant pressure is desired in the operation of accumulator 10. In an embodiment, the constant pressure is at atmospheric pressure. Further, without being limited by theory, a constant pressure is desired to eliminate the number of pumping, measuring, and regulating devices involved with pressurized systems. Chamber separator 35 and flexible bag 165 may be composed of any material that is flexible but non-elastic. Without limitation, examples of suitable materials for chamber separator 35 and flexible bag 165 include high density polyethylene or MYLAR, which is a registered trademark of E.I. Du Pont de Nemours and Company. In alternative embodiments, chamber separator 35 and flexible bag 165 may have a minimum amount of elasticity. In such alternative embodiments, chamber separator 35 and flexible bag 165 may be composed of any flexible and non gas permeable materials that exhibit elasticity. In some embodiments, the materials of chamber separator 35 and flexible bag 165 are selected based on the chemical nature of the gases involved and compatibility therewith.

Figure 4:
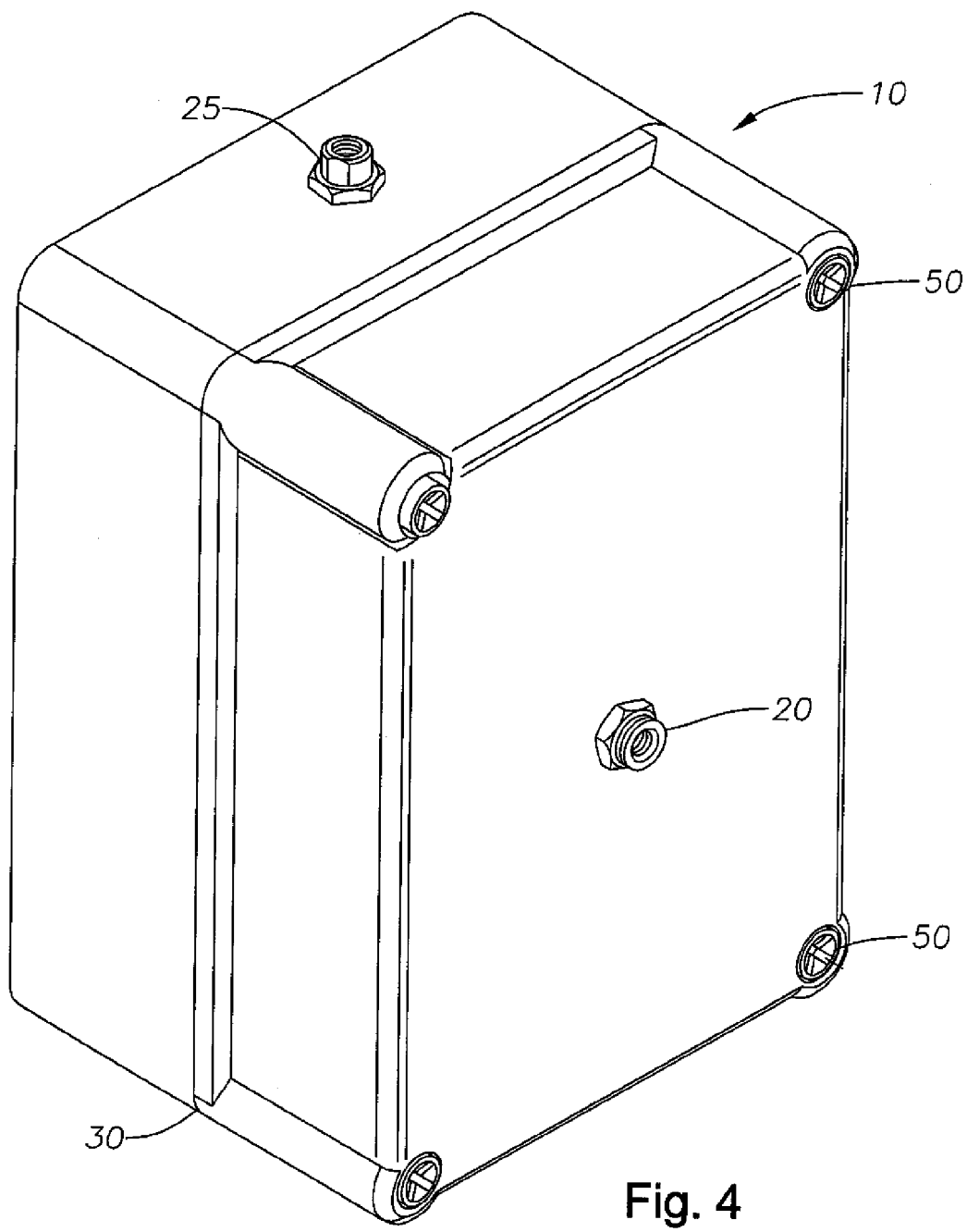
FIG. 4 illustrates an accumulator.

As shown in FIGS. 1-3, chamber 30 is composed of any materials suitable for supporting chamber separator 35. Without limitation, chamber 30 may be composed of acrylonitrile-butadiene-styrene (ABS), polycarbonate, polymethyl methacrylate (PMMA), aluminum, steel, plastic, or any combination thereof FIG. 4 illustrates a perspective view of accumulator 10 showing chamber 30 having a sample orifice 20 and a purge gas orifice 25. Sample orifice 20 may have any size and configuration suitable for allowing sample gas 105 to be introduced and exit accumulator 10. Purge gas orifice 25 may have any size and configuration suitable for allowing purge gas to be introduced and exit accumulator 10. It is to be understood that FIG. 4 illustrates one sample orifice 20 and one purge gas orifice 25. However, accumulator 10 is not limited to one of orifices 20, 25 but instead may include more than one of each. In an embodiment as illustrated in FIG. 4, chamber 30 is composed of two portions that are secured to each other by securing means 50. Securing means 50 may include any securing means suitable for securing the two portions to each other, such as screws. Chamber 30 is not limited to the configuration and design of FIG. 4 but instead may have any other suitable design and configuration for allowing the transfer of sample gas 105 at constant pressure.

As further illustrated in FIGS. 1 and 3, sample gas collection apparatus 15 may include any method and apparatus for collecting a sample gas from a solid, liquid, or gas sample. Without limitation, examples of suitable methods for sample gas collection apparatus 15 include combustion, chemical reaction, catalytic reactions, and the like. Combustion may be accomplished by any suitable method such as by a combustion furnace. FIGS. 1 and 3 illustrate embodiments in which sample gas collection apparatus 15 is a combustion furnace for combusting a solid sample 85. The combustion furnace is not limited to the combustion furnace configuration illustrated in FIGS. 1 and 3 but instead may include any configuration for collecting a sample gas.

In an embodiment of the operation of sample analysis process 5 as illustrated in FIG. 1 in which sample gas collection apparatus 15 is a vertical combustion furnace, combustion tube 80 is lifted into the furnace and combines with riser tube holder 95 to create a combustion chamber sealed against intrusion of atmospheric air or any other outside contaminants. Gas supply 60 provides a gas 65 to sample gas collection apparatus 15. In an embodiment, gas supply 60 is a pressurized gas supply. Gas 65 is any combustion gas suitable for use in combustion of sample 85. Without limitation, examples of gas 65 include oxygen, air, and the like. In some embodiments, gas 65 is fed through a valve 70 and flow restrictor 75 through riser tube, which may control the flow of gas 65 to sample gas collection apparatus 15. Flow restrictor 75 is any flow restrictor such as a sintered metal frit that is suitable for restricting the flow of sample gas collection apparatus 15. In alternative embodiments, sample analysis process 5 does not include valve 70 and/or flow restrictor 75. Gas 65 is fed to sample gas collection apparatus 15 through riser tube 90 to create an oxygen rich environment inside the furnace in which combustion takes place to combust sample 85, which is disposed on riser tube 90. Sample gas 105 flows out of sample gas collection apparatus 15 and into sample side 40 of accumulator 10. In some embodiments, sample gas 105 flows through catalyst in the end of the combustion chamber. Sample gas 105 includes the oxygen from gas 65 and the products of combustion. In some embodiments, sample gas 105 may be passed through water removal apparatus 110 prior to being fed to accumulator 10. Water removal apparatus 110 may be any device suitable for removing water or any other liquid from sample gas 105. For instance, water removal apparatus 110 may be a particulate filter, a condensation trap, or the like.

In the embodiment illustrated in FIG. 1, accumulator 10 includes chamber separator 35. In embodiments, accumulator 10 operates at atmospheric pressure. Accumulator 10 has valve 170 that connects pressure side 45 to vent 120. Vent 120 is a vent to the atmosphere. When sample gas 105 is fed to accumulator 10, valve 170 is open to vent 120, which allows any gas in pressure side 45 to escape accumulator 10 and thereby prevents the increasing volume of sample gas 105 in sample side 40 from resulting in an increased pressure in accumulator 10. By allowing the sample volume to increase without an increase of pressure in accumulator 10, sample gas 105 may be fed to accumulator 10 at low pressures. Advantages of such atmospheric accumulation include allowing sample capture with a minimum number of pumps, regulators and flow control devices in the sample feed stream (i.e., sample gas 105). Without limitation, such additional components, if used, may lead to interferences (i.e., degradation) of the chemical compositions of sample gases and/or damage to the delicate and precision flow control devices, which may be caused by the nature of the sample gas streams. For instance, sample gas 105 may be corrosive and/or particulate bearing. In alternative embodiments (not illustrated), accumulator 10 may be operated at higher than atmospheric pressures. For instance, a backpressure regulator may be added between pressure side 45 and vent 120 to provide a constant, above atmospheric pressure. Advantages of higher than atmospheric pressures (i.e., compression) include allowing larger sample volume to be collected with a much smaller container (i.e., accumulator 10).

Figure 5:
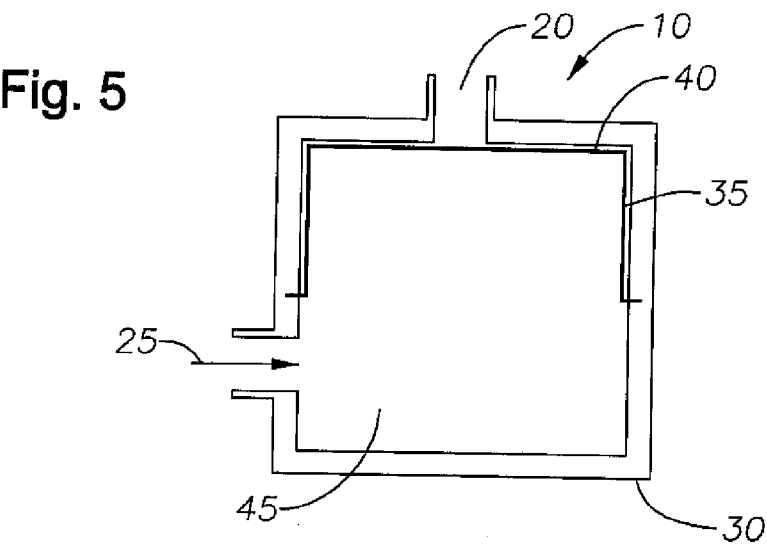
FIG. 5 illustrates a cross sectional side view of an embodiment of an accumulator in which the accumulator is purged by a purge gas.
Figure 6:
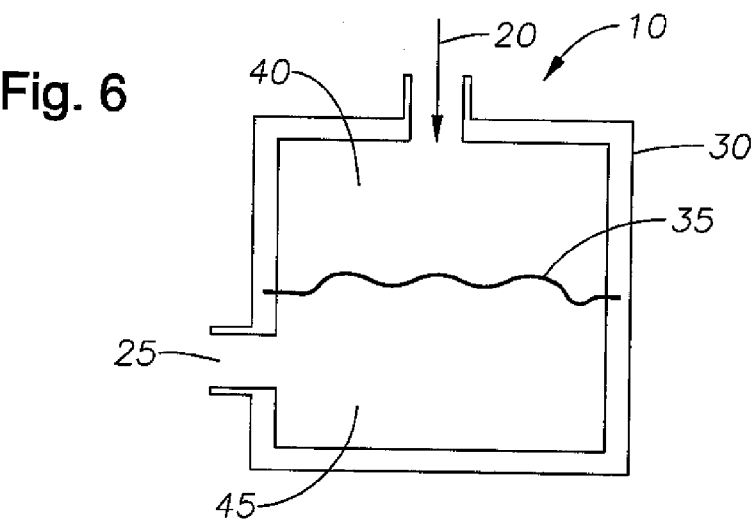
FIG. 6 illustrates a cross sectional side view of an embodiment of an accumulator in which a sample is being added to the accumulator.
Figure 7:
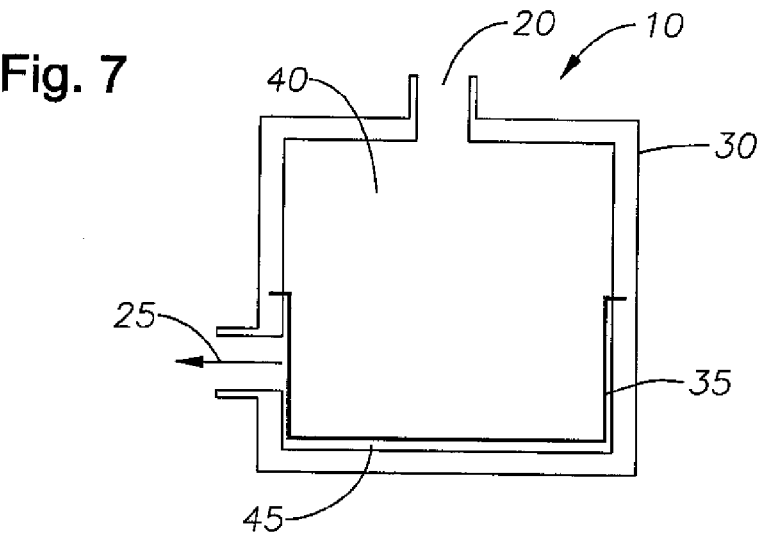
FIG. 7 illustrates a cross sectional side view of an embodiment of an accumulator in which the accumulator is about full of sample gas.

FIGS. 5-7 illustrate adding volume of sample gas 105 to an embodiment of accumulator 10 as illustrated in FIG. 1 in which accumulator 10 has chamber separator 35. In the embodiment of FIG. 5, accumulator 10 is substantially full of gas on pressure side 45 with no sample gas 105 on sample side 40. In such an embodiment, accumulator 10 has about no volume on sample side 40. FIG. 6 illustrates an embodiment in which a volume of sample gas 105 is being added to accumulator 10 with chamber separator 35 preventing sample gas 105 from flowing to pressure side 45. FIG. 7 illustrates an embodiment in which accumulator 10 is about full of a volume of sample gas 105 with no sample gas 105 flowing out of accumulator 10 through pressure side 45.

As further illustrated in FIG. 1, when collection of the desired sample volume of sample gas 105 is complete, valve 115 isolates sample side 40 from sample gas collection apparatus 15 (i.e., the combustion furnace). Valve 130 is switched to open accumulator 10 to analyzer 150, and a measured aliquot is pulled from accumulator 10 to analyzer 150. Analyzer 150 may pull multiple aliquots of the same volume or different volumes of sample gas 105 from accumulator 10. In some embodiments, sample gas 105 is stored in accumulator 10 until it is desired for analysis. Analyzer 150 may include any analyzer suitable for analyzing a gas sample. Analyzer 150 analyzes a desired component of sample gas 105. For instance, the analysis may include determining the amount of a component in sample gas 105. The component may be any desired component such as carbon (i.e., total carbon analysis), nitrogen (i.e., total nitrogen analysis), sulfur, and the like. In an embodiment, analyzer 150 measures the amount of carbon in sample gas 105.

As further illustrated in FIG. 1, when it is desired that no more of sample gas 105 from accumulator 10 is to be analyzed, sample side 40 may be purged of sample gas 105. Purging of sample side 40 includes switching valve 130 to open sample side 40 to vent 120. In addition, valve 170 is switched to pressurize pressure side 45, which purges sample side 40 of sample gas 105. FIG. 1 illustrates an embodiment in which pressure side 45 is pressurized by the same gas 65 that is fed to sample gas collection apparatus 15. In alternative embodiments (not illustrated), pressure side 45 is pressurized by a different gas than gas 65. Pressurization of pressure side 45 purges sample side 40 by increasing the pressure and volume on pressure side 45, which reduces the volume in sample 40 and forces sample gas 105 out of accumulator 10 and to vent 120. After purging sample side 40 of sample gas 105, valve 170 is switched back to vent 120, valve 130 is switched away from vent 120 and closed. In some embodiments, valve 135 is switched to allow gas 65 (or another purge gas) to flow into sample side 40 for a purge of sample side 40. Valve 135 is then closed to the flow of gas 65, valve 130 is opened to vent 120, and valve 170 is opened to allow the flow of gas 65 to fill pressure side 45 and purge sample side 40 of gas 65. In an embodiment, a timer controls the amount of sample gas 105 and gas 65 fed to sample side 40 and pressure side 45 during sample analysis process 5. In an embodiment in which accumulator 10 includes flexible bag 165 disposed in chamber 30, the same operation steps as described for the above operation of the embodiment of accumulator 10 having sample side 40 and chamber separator 35 apply, with it to be understood that flexible bag 165 operationally takes the place of both the sample side 40 and chamber separator 35.

In an embodiment of the operation of sample analysis process 5 as illustrated in FIG. 3 in which accumulator 10 is a flexible bag 165, valve 130 is opened to vacuum 160, and vacuum 160 removes any gas in accumulator 10. When it is desired for sample gas 105 to be fed to accumulator 10 from sample gas collection apparatus 15, valve 130 is closed, and sample gas 105 is fed to accumulator 10. When collection of the desired volume of sample gas 105 is complete, valve 115 is switched to isolate sample gas 105 in accumulator 10 from sample gas collection apparatus 15 (i.e., the combustion furnace). Valve 130 is switched to open accumulator 10 to analyzer 150, and a measured aliquot is pulled from accumulator 10 to analyzer 150. Analyzer 150 may pull multiple aliquots of the same volume or different volumes of sample gas 105 from accumulator 10. In some embodiments, sample gas 105 is stored in accumulator 10 until it is desired for analysis. When it is desired that no more of the sample gas 105 in accumulator 10 is to be analyzed, accumulator 10 may be purged of sample gas 105. Purging of accumulator 10 includes switching valve 130 to open flexible bag 165 to vacuum 160, which purges accumulator 10 of sample gas 105. In some embodiments, accumulator 10 may then be flushed by the same gas 65 or by a different gas. In such embodiments, after vacuum 160 purges accumulator 10 of sample gas 105, valve 130 is closed, and valve 135 allows gas 65 to feed into accumulator 10. After the desired amount of gas 65 is fed to accumulator 10, valve 135 closes the flow of gas 65, and valve 130 is opened to vacuum 160, which purges accumulator 10 of gas 65. In an embodiment, a timer controls the amount of sample gas 105 and gas 65 fed to accumulator 10 during sample analysis process 5.

In alternative embodiments, sample analysis process 5 may also include valve 100, which allows a backflow of gas 65 to prevent combustion tube 80 from being contaminated with atmospheric carbon dioxide. In some of such alternative embodiments, gas 65 may flow through a flow restrictor 125 before valve 100.

It is to be understood that the embodiments of FIGS. 1 and 3 include using flow restrictors 75, 125 to set timed flow rates for a known amount of gas, but that sample analysis process 5 is not limited to use of such flow restrictors 75, 125. Instead, any other desirable method may be used in combination with or instead of flow restrictors 75, 125. For instance, pressure and temperature sensors, heaters, and flow controllers may be used for precise control and data logging purposes.

In alternative embodiments (not illustrated), sample analysis process 5 does not include sample gas collection apparatus 15 but instead the desired sample gas 105 to be analyzed is provided and fed to accumulator 10 with sample analysis process 5 operating otherwise as described above.

In other alternative embodiments, chamber separator 35 and flexible bag 165 are elastic. In such alternative embodiments, sample side 40 and flexible bag 165 are not fully filled with sample 105, which prevents elastic deformation of chamber separator 35 and flexible bag 165 from sample gas 105 and allows a constant pressure in accumulator 10.

Therefore, sample analysis process 5 including accumulator 10 provides the advantage of regulating the amount of sample gas 105 passed to analyzer 150. Additional advantages include the ability to store sample gas 105 for analysis at a later time. Further advantages provided include adjusting the size of samples (i.e., the aliquots) fed to analyzer 150 as well as allowing repeated samples of the same size to be fed to analyzer 150. For instance, in some embodiments, small aliquots of sample gas 105 may be desired for analysis for high carbon content, and large aliquots of sample gas 105 may be desired for low carbon content. Consequently, sample analysis process provides a reservoir (i.e., accumulator 10) to provide a broad range of sample sizes for a multitude of measurements.

Although the present invention and its advantages have been described in detail, it should be understood that various changes, substitutions and alterations may be made herein without departing from the spirit and scope of the invention as defined by the appended claims.

What is claimed is:

1. A method for capturing a sample gas for analysis, comprising:
   (A) feeding an increasing volume of the sample gas to a flexible bag that is impermeable to gas;
   (B) withdrawing a first aliquot of the sample gas from the flexible bag;
   (C) feeding the first aliquot of the sample gas to an analyzer;
   (D) analyzing a desired component of the sample gas; and
   (E) withdrawing a second aliquot of the sample gas from the flexible bag.

2. The method of claim 1 wherein the volume of sample gas in the second aliquot is different from the volume of sample gas in the first aliquot.

3. The method of claim 1 wherein the flexible bag has a variable volume.

4. The method of claim 1 further comprising combusting a sample to produce the sample gas.

5. The method of claim 1 further comprising coupling the flexible bag to the analyzer before the sample gas is fed to the flexible bag.

* * * * *